US010398818B2

(12) United States Patent
Wiesener et al.

(10) Patent No.: US 10,398,818 B2
(45) Date of Patent: *Sep. 3, 2019

(54) IMPLANTABLE HEART PUMP (71) Applicant: Berlin Heart GmbH, Berlin (DE)

(72) Inventors: Constantin Wiesener, Potsdam (DE);
Dominik Karch, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/111,698

(22) Filed: Aug. 24, 2018

(65) Prior Publication Data
US 2018/0361044 A1 Dec. 20, 2018

Related U.S. Application Data (63) Continuation of application No. 15/182,898, filed on Jun. 15, 2016, now Pat. No. 10,080,828.

(30) Foreign Application Priority Data

Jun. 16, 2015 (EP) ..................... 15172410

(51) Int. Cl.
A61M 1/10 (2006.01)
A61M 1/12 (2006.01)
A61N 1/365 (2006.01)

(52) U.S. Cl.
CPC ........ *A61M 1/1086* (2013.01); *A61M 1/1015* (2014.02); *A61M 1/12* (2013.01); *A61N 1/36514* (2013.01); *A61M 1/101* (2013.01); *A61M 1/1013* (2014.02); *A61M 1/1031* (2014.02); *A61M 1/122* (2014.02); *A61M 1/127* (2013.01); *A61M 2205/332* (2013.01); *A61M 2205/3303* (2013.01); *A61M 2205/3313* (2013.01); *A61M 2205/3334* (2013.01);
(Continued)

(58) Field of Classification Search
CPC .. A61M 2205/3306; A61M 2205/3379; A61M 2205/3389; A61M 2205/3334; A61M 2205/205; A61M 1/1008; A61M 1/1086; A61M 1/1031
See application file for complete search history.

(56) References Cited

U.S. PATENT DOCUMENTS 5,924,975 A 7/1999 Goldowsky
5,964,694 A 10/1999 Siess et al.
(Continued)

FOREIGN PATENT DOCUMENTS

EP 2 564 771 A1 3/2013
WO WO 91/08004 6/1991
(Continued)

*Primary Examiner* — George R Evanisko
(74) *Attorney, Agent, or Firm* — Brinks Gilson & Lione (57) ABSTRACT A heart pump and method for the operation of a heart pump are provided. A volume flow and an oxygen saturation may be determined by a sensor device. The sensor device including an oximeter configured to determine the oxygen saturation from blood. The oximeter may be fastened on the pump and include a ring on which a radiation source and a radiation sensor are fastened. Oxygen flow through the pump may be determined from the volume flow and the oxygen saturation. The heart pump may be controlled based on the oxygen saturation and/or the oxygen flow through the pump.

15 Claims, 3 Drawing Sheets (52) U.S. Cl.
CPC .............. *A61M 2205/3365* (2013.01); *A61M 2205/3379* (2013.01); *A61M 2230/205* (2013.01)

(56) References Cited

U.S. PATENT DOCUMENTS

| | | |
|---|---|---|
| 10,080,828 B2 * | 9/2018 | Wiesener ............ A61N 1/36514 |
| 2003/0128125 A1 | 7/2003 | Burbank et al. |
| 2004/0152945 A1 | 8/2004 | Kantrowitz et al. |
| 2005/0196293 A1 | 9/2005 | Ayre et al. |
| 2011/0118537 A1 | 5/2011 | Wampler |
| 2013/0303831 A1 | 11/2013 | Evans |
| 2014/0275720 A1 | 9/2014 | Ferrari |
| 2015/0141911 A1 | 5/2015 | Bulent et al. |

FOREIGN PATENT DOCUMENTS

| | | |
|---|---|---|
| WO | WO 2011/056980 A2 | 5/2011 |
| WO | WO 2011/056980 A3 | 5/2011 |

* cited by examiner

IMPLANTABLE HEART PUMP

CROSS-REFERENCE TO RELATED APPLICATIONS

This application is a continuation of U.S. non-provisional patent application Ser. No. 15/182,898, filed Jun. 15, 2016, which claims priority under 35 USC § 119 to European patent application 15172410.1 filed Jun. 16, 2015. The entire contents of each of the above-identified applications are hereby incorporated by reference.

DETAILED DESCRIPTION

This intellectual property right lies in the field of medical technology and in particular relates to heart pumps as well as to assistance systems for patients with an insufficient or defect heart function.

Implantable pumps and ones which are outside the body, for assisting and supplementing the heart function when delivering blood, have been widespread and developed for some while now in the state of the art. Control systems which on the one hand determine the necessity for assistance and on the other hand set the degree given to the patient's heart, also belong to this state of the art, wherein challenging tasks for example lie in determining and setting the actual volume flow through the pump.

Such pumps are often designed as rotor pumps with a rotating delivery device with delivery elements in the form of blades, by which means a radial pump or an axial pump can be formed. With such pumps, the actual volume flow is usually determined from technical operating parameters of the pump, such as for example the speed of the rotor, the torque or an axial bearing strain of a thrust bearing, with the help of families of characteristics curves. The consideration of a further parameter, specifically the oxygen saturation of the delivered blood or the volume flow of oxygen-saturated blood is helpful for the control of the assistance system. Measured arterially (LVAD), this parameter depends on how well the pulmonary system functions for the absorption of oxygen. The arterial saturation reduces e.g. in the case of a pulmonary oedema. In the case of a RVAD, the mixedly/centrally venous oxygen saturation, measured in the right atrium or ventricle, can moreover be used for recognising physical load/stress conditions.

Measuring devices for determining the oxygen saturation in the blood have already been known from the state of the art for some time now. Here, the method of optical pulse oyxmetry is to be emphasised, with which method a pulse oxymeter beams through blood located in the tissue (for example in a finger or earlobe) with a light beam in two wavelength regions. Herein, one utilises the fact that oxygenated and non-oxygenated haemoglobin have different absorption spectra. The quotient of two absorption values in the different wavelength regions is formed, and thus the ratio of the distribution density of the oxygenated and non-oxygenated haemoglobin in the tissue and thus in the blood is determined.

The use of an oxygen sensor in combination with an implantable cardial therapy apparatus is already known for example from the European patent EP 2 570 143 B 1.

Against the background of the state of the art, it is the object of the present invention to combine a device for determining the oxygen saturation of the blood of a patient with a heart assistance system, in a manner such that a simple handling is combined with a reliable measurement accuracy and good reproducibility of the measurement.

The object is achieved by an implantable heart pump according to patent claim 1. Patent claims 2 to 6 specify embodiments of the invention. Patent claims 7 and 8 relate to a pump device with an implantable heart pump, and patent claim 9 specifies a method for operation of a heart pump. The dependent claims 10 to 11 specify embodiments of the operating method.

What is described therefore is an implantable heart pump with a delivery channel and with a delivery device for blood, said delivery device being arranged in this delivery channel. The object is achieved by a first sensor device for measuring the oxygen saturation of the blood, said first sensor device being fastened on the heart pump, in particular on a wall of the delivery channel, further in particular on a pump tube, in which the delivery channel at least partly runs.

An effect of this is that the oxygen saturation of the blood or, expressed differently, the share of oxygen-saturated haemoglobin molecules with respect to the total number of haemoglobin molecules in the blood, is detected directly at the pump. Such pumps usually lie in the direct proximity of the heart and often suck the blood also directly out of a ventricle. Inasmuch as this is concerned, it can be ensured that the detected oxygen saturation of the blood corresponds to the value in the respective ventricle. Moreover, the volume flow can be determined by the pump, so that together with the oxygen content, as a whole the oxygen flow through the pump can be determined in a precise manner. The components of the heart pump on which the first sensor device can be fastened moreover do not change with regard to the design, so that the basic conditions for oxygen measurement are reproducible. This for example would not be fulfilled with the same reproducibility if the first sensor device were arranged in the patient body independently of the heart pump.

A further effect lies in the fact that the detected, in particular the venous oxygen content of the blood can also be used directly for the control and/or regulation (closed-loop control) of the heart pump. A post-adjustment or calibration of the measurement is not necessary due to the integration of the sensor device into the heart pump, and also the connections to a control apparatus of the pump can be created in a simple and reliable manner, in particular before the implantation.

A further design envisages the first sensor device comprising at least one, in particular two radiation sources, as well as at least one, in particular two radiation sensors. The measurement, just as the construction of the sensor, is based on the known principle of pulse oxymetry, which describes the oxygen saturation by way of the measurement of a light absorption and light reflection or light transmission. This is based on the knowledge that oxygenated and non-oxygenated haemoglobin have different light absorption spectra. Accordingly, it is possible to measure the light transmission of the blood at the first sensor device by measuring the light absorption in at least two wavelength regions (typically in the 660 nanometer and 940 nanometer region), and to put the light intensities in relation with one another by way of quotient formation, in order to determine the share of oxygenated haemoglobin molecules with respect to the number of non-oxygenated molecules or to the total (i.e. oxygenated and non-oxygenated) haemoglobin molecules. In this context, the total density of the haemoglobin molecules in the examined volume is of no significance.

The mentioned measuring method has been tried and tested and is sufficiently reliable and accurate in order to be able to arterially (LVAD) and venously measure respective typical physiological values in a sufficiently accurate manner, in the case of a healthy and a sick patient.

Semiconductor diodes (infrared region/red region) are usually used as radiation (beaming) sources, and a phototransistor for example as a radiation sensor.

A further design can envisage the radiation sensor detecting the radiation intensity in at least two different wavelength regions, independently of one another. In the mentioned case, the system may apply two radiation sources in the form of different diodes, but only a single radiation sensor with a known sensitivity in the applied wavelength regions. However, it is also conceivable to apply different radiation sensors for detecting the radiation of the two radiation sources.

A further embodiment envisages the connection path between the radiation source/radiation sources and the radiation sensor lying transversely, in particularly perpendicularly, to the flow direction of the blood in the delivery channel. The radiation sources and the radiation sensors can be simply arranged outside the blood flow or at the edge of the blood flow with such a design.

An optimised covering of the complete blood flow and an as good as possible utilisation of the absorption is achieved, according to one embodiment, by way of the radiation source and the radiation sensor lying opposite one another on the periphery of the pump tube.

The implementation can moreover envisage a second sensor device for the bearing strain of a magnetic thrust bearing of a pump rotor and/or a sensor device for detecting the torque transmitted onto the rotor, and/or the rotation speed. The torque of the pump rotor can be determined for example from the pump flow, i.e. the current strength of an electric motor driving the pump rotor. In particular, variables such as volume flow and pressure difference across the pump can be determined by simultaneously measuring the bearing strain and/or the rotation speed and/or torque, and these variables are closely related to the physiological parameters of the patient. The obtained information with regard to oxygen saturation can thus be processed further together with data concerning the blood flow to further meaningful data.

As the case may be, a computation of blood viscosity, and thus also of the haematocrit in the blood, is possible in the case of acquiring a sufficient number of parameters.

The considerations moreover relate to a pump device with a pump of the type described above as well as with a control device or an analysis device, said devices being connected to the first sensor device as well as to the third sensor for detecting the speed of a pump rotor.

Moreover, with such a pump device, one can envisage the control device being connected to a sensor for the volume flow and/or the detection of the pump flow and of the speed of a motor driving the pump rotor and/or to a sensor for detecting the bearing strain of a magnetic thrust bearing mounting the pump rotor.

If the measurement data with regard to the oxygen saturation of the blood as well as with regard to the speed of the pump and to the thrust bearing strain and/or to a torque of the pump rotor are transferred to the control device, then the volume flow of the blood through the pump, the oxygen content and thus also the oxygen flow through the pump into the body of the patient, in particular when the aortic valve/pulmonary valve of this patient does not open and the pump flow thus corresponds to the cardiac output, can be computed in the control device. In this latter case, the cardiac output as well as the venous and arterial saturation can be measured in a BiVAD configuration, and the oxygen consumption of the patient can therefore be deduced.

Different physiological conditions of the patient, such as the physical stress of the patient, can be determined from the oxygen situation, in particular venous oxygen saturation. Accordingly, the pump can be controlled in accordance with the physical stress and with a desired optimised oxygen content.

A sensor for detecting the volume flow through the pump may also be provided with a pump device with a pump of the type mentioned above.

Moreover, an acceleration sensor can be provided in the region of the heart pump, in order to check at least approximately the respective oxygen saturation data against a potential bodily movement and the physiological stress (loading) of the patient entailed by this, for plausibility checks.

The present embodiments, apart from an implantable heart pump and a pump device of the type described above, also relate to a method for operation of an implantable heart pump, wherein the volume flow and the oxygen saturation are evaluated by sensor devices directly on the pump and the oxygen flow through the pump is continuously determined from this.

The determined values can be linked with a high accuracy and reliability, and for example the oxygen flow through the pump determined, due to the simultaneous evaluation of the oxygen content of the blood and the volume flow of the pump under the same basic conditions. The energy supply for the first sensor, which measures the oxygen content of the blood, can be derived directly from the energy supply of the heart pump, for example the energy supply of the motor or the other sensors. The cables for the connection of the sensors to a control appliance may bundle all leads of the sensors arranged on the pump with one another, in a manner such that all leads are connected to one another and enveloped by a common cable sheath. Disturbances or interactions of individual leads with the tissue can be minimised by way of this.

The method according to the invention can advantageously be designed such that the control/regulation of the speed or of the volume flow through the pump is based on the determined oxygen saturation or the determined oxygen flow through the pump. For example, it may be tried to increase the delivered volume by increasing the rotational speed in order to supply the body of the patient as sufficiently as possible with oxygen in the case that a low oxygen flow through the pump is measured.

One can also envisage an indicator being determined from the oxygen saturation of the blood and/or and degree of assistance given to the patient's heart.

Figure 6:
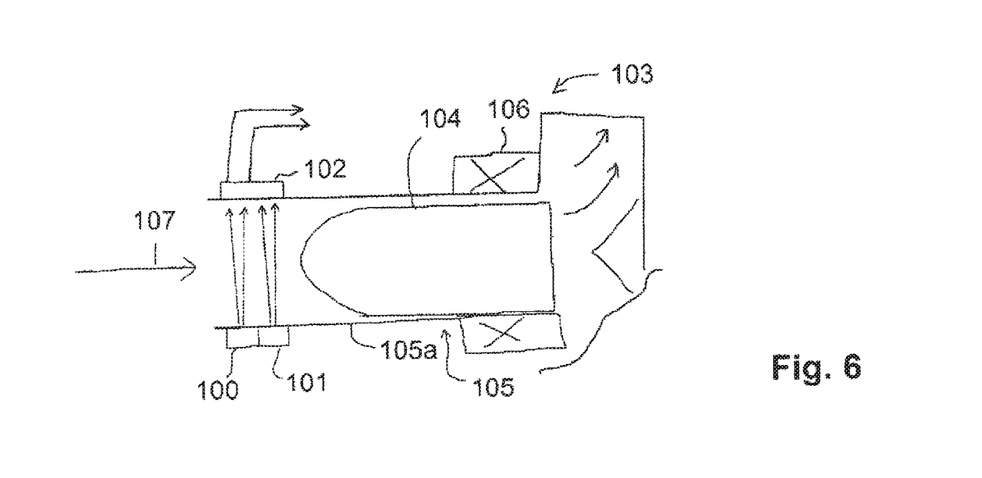
FIG. 6 is a schematic diagram of the construction of a pump, in whose pump pipe a pulse oxymetry device is integrated.
Figure 7:
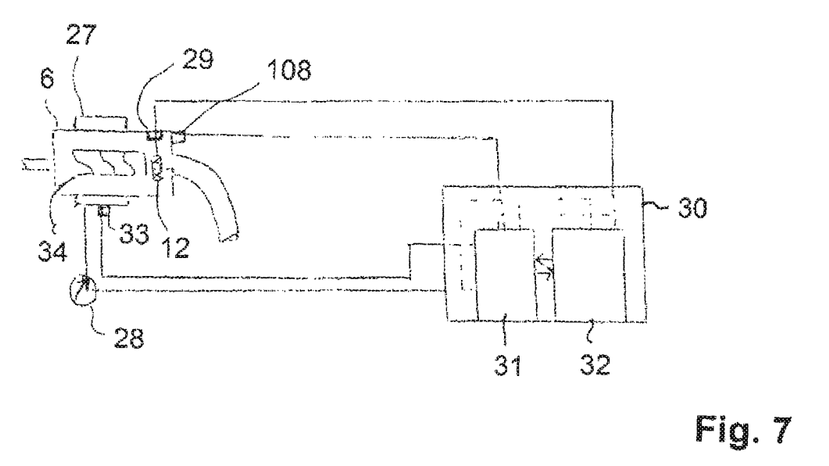
FIG. 7 is a schematic diagram of the construction of a pump device.

In the following, exemplary embodiments are shown by way of figures of a drawing, and explained hereinafter. There is shown in FIG. 1 schematically, the view of a patient body with the heart of a patient and a VAD (ventricular assist device) pump, FIG. 2 in a three-dimensional view and schematically, an axial rotor pump, FIG. 3 in a schematic lateral view, the housing of an axial pump with a rotor, with a drive and with a magnetic thrust bearing, FIG. 4 a typically family of characteristic curves of a pump, with characteristic curves which permit an assignment of a speed and a pressure difference to a volume flow, FIG. 5 a diagram according to FIG. 4, by way of which an evaluation of the pressure difference across the pump is explained by way of two different methods and the comparison of the results, FIG. 6 schematically, the construction of a pump, in whose pump pipe a pulse oxymetry device is integrated, as well as FIG. 7 schematically, the construction of a pump device for application of the method according to the invention.

Figure 1:
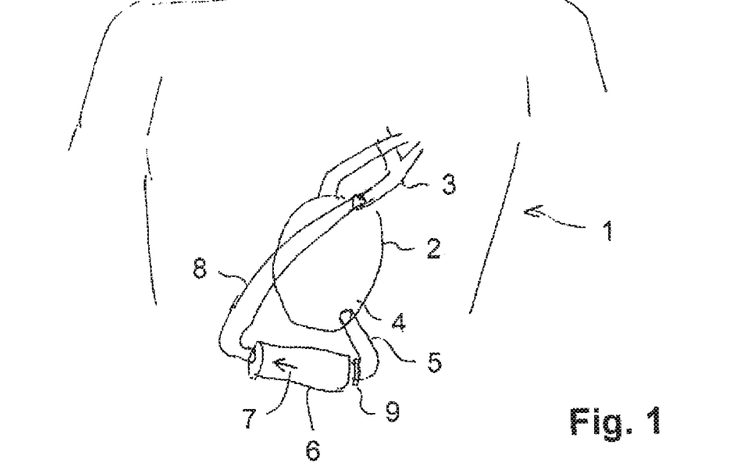
FIG. 1 is a schematic view of a patient body with the heart of a patient and a VAD (ventricular assist device) pump.

FIG. 1 shows an upper body of a patient 1 with the heart 2 of the patient and with a part of the aorta 3. An inlet branch 5 of an implantable VAD pump (ventricular assist device) 6 is connected to a ventricle 4 of the heart, and this pump sucks blood out of the ventricle 4 in the direction of the arrow 7 to the inlet of the pump and delivers this from the outlet of the pump via the outlet cannula 8 directly into the aorta 4.

Such pumps can significantly assist the pump function of a bad heart or one which is not fully functioning. This can be envisaged as a temporary therapy or as a permanent therapy. Here, the use of axial rotor pumps which deliver blood in the axial direction 7 by way of a rapidly rotating rotor has been found to be particularly advantageous. Such pumps are usually driven by an electromotoric drive which is in the region of the pump casing and which can be fed by an accompanying battery or a stationary electricity connection.

It is necessary to determine and track the volume throughput through the pump in order to be able to control physiological parameters of the patient as well as the operating condition of the pump to a sufficiently accurate extent. In principle, different methods are known for this, which, for example, include detection of the speed of the rotor and the pressure difference across the rotor. The evaluation of the volume flow is also possible by way of the speed of the pump. Finally, the volume throughput can also be determined by way of taking into account the speed of the pump rotor and the torque acting upon the rotor, or the speed of the pump rotor and the bearing strain in a thrust bearing of the rotor.

Figure 2:
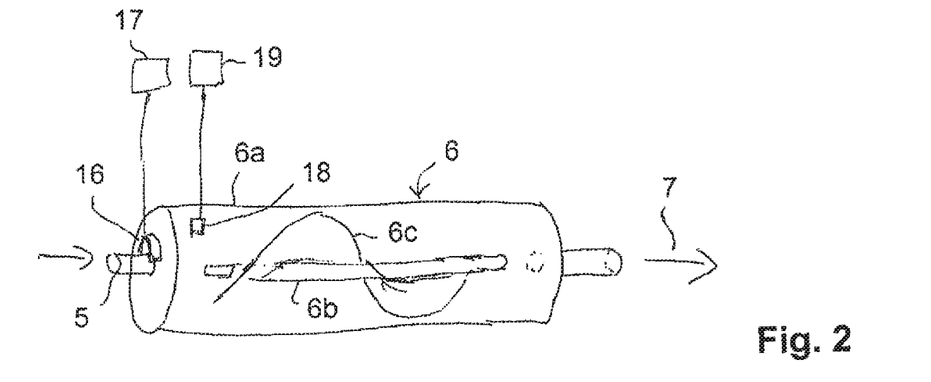
FIG. 2 is a three-dimensional schematic view of an axial rotor pump.

An axial pump 6 with a hub 6b which is mounted in a casing 6a and on which one or more delivery elements 6c, for example in the form of a revolving, helical delivery blade are fastened, is schematically represented in FIG. 2. The fluid to be delivered, which is to say the blood, is delivered in the casing 6a in the direction of the arrow 7 by way of rotation of the rotor. A hub does not necessarily need to be provided if the rotor is mounted in a magnetic thrust bearing. In this case, it is merely necessary to shape, arrange and hold the delivery elements of the rotor in a suitable manner.

Figure 3:
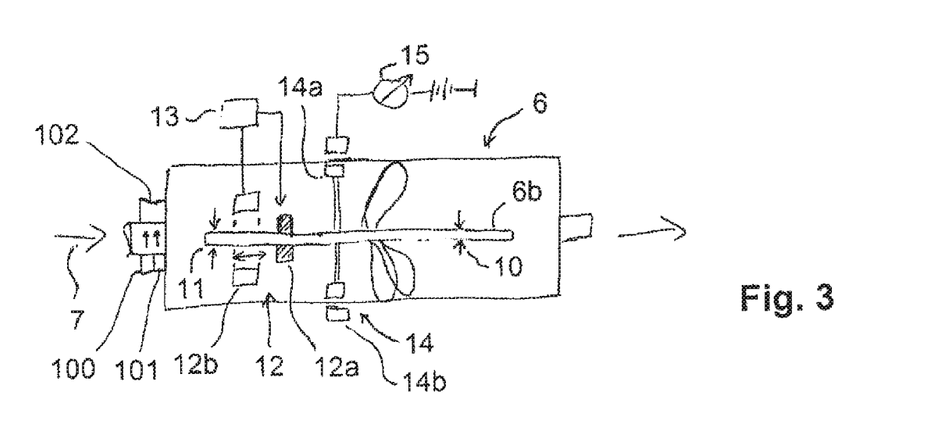
FIG. 3 is a schematic lateral view showing a housing of an axial pump with a rotor, with a drive and with a magnetic thrust bearing.

The mounting and the drive of the rotor of the pump 6 is represented in FIG. 3 in a more detailed, but schematic manner. Firstly, in the region of the hub 6b, a first radial bearing is symbolically represented and indicated with the reference numeral 10, whereas a second radial bearing is likewise symbolically represented and indicated with 11. The second radial bearing 11 can be combined for example with a magnetic thrust bearing 12, but can also be constructed separately from this.

The thrust bearing 12 is designed as a controllable magnetic thrust bearing, wherein a first annular magnet 12a is connected to the hub 6b or, if the rotor is designed without a hub, is connected to the rotor and rotates with this hub/rotor.

A second, annular magnet or annular arrangement of individual magnets 12b is arranged in the housing 6a of the pump 6 in a stationary manner and surrounds the hub 6b or a part of the rotor. An axial force which acts upon the rotor and which is opposite to the flow direction 7 of the fluid through the pump as a reaction force arises due to the repulsion of the stationary magnet 12b or the stationary magnet arrangement 12b on the one hand and the rotating magnet 12a on the hub 6b on the other hand.

The thrust bearing 12 comprises a second sensor for detecting the axial position of the magnet 12a fastened on the hub, for example with eddy current sensors, wherein the information on the axial position is transferred to a control device 123 for example in the form of a voltage measured by the sensors. The control loop of the magnet bearing 12 can be closed by way of this, and the control device 13 can closed-loop control the axial position of the magnet 12a, and thus of the rotor or the hub 6b, to a constant size. The force which is accommodated by the thrust bearing in the process can be determined by the current strength applied by the control device 13 or the voltage measured in the eddy current sensors.

The force which is accommodated by the thrust bearing in the case of a non-regulated bearing may also be determined by way of measuring the axial deflection of the hub against the magnetic force of the thrust bearing.

An electric motor 14, for which for example permanent magnets 14a which are fixedly connected to the rotor and a stator 14b which is connected to the pump casing 6a may be envisaged, is schematically represented in FIG. 3. A brushless electric motor is thus realised by way of suitable activation of the stator windings. The current strength to which the stator 14b is subjected can be measured by way of a measuring appliance 15, and the produced torque which is applied onto the rotor can be determined from this current strength in a simple manner.

Moreover, FIG. 3 in the region of the pump casing on a pump inlet branch shows a first sensor device 100, 101, 102 which comprises a first radiation source in the form of a diode 100, as well as a second radiating diode 101 and a phototransistor 102 as a radiation sensor which can detect the radiation of both diodes. The first diode 100 can radiate or beam for example at a wavelength of 660 nanometers, whereas the second diode 101 radiates at 940 nanometers. The radiation sources lie diametrically opposite the radiation sensor, on the periphery of the pump inlet branch. At least parts of the pump inlet branch are either provided with openings for through-beaming which are covered by the sensors and the radiation sources, or are manufactured of a transparent material. The absorption and thus the concentration ratio of the molecules which preferably absorb the respective wavelength (oxygenated and non-oxygenated haemoglobin molecules in the case of oxygen saturation measurement) can be determined from the absorption coefficients of the blood in the individual wavelength regions.

A normalisation simultaneously takes place by way of quotient formation of the concentration values which results in the oxygen saturation. Despite this, a calibration of the sensor device makes sense, in particular if radiation passes through a transparent part of the pump inlet branch or of a pump tube when measuring.

The saturation results from the equation:

$$S_pO_2 = \frac{HbO_2}{(HbO_2 + Hb)}$$

Therein, $S_pO_2$ is the oxygen saturation, Hb the concentration of the non-oxygenated haemoglobin, and $HbO_2$ is the concentration of the oxygenated haemoglobin. The concentrations can be determined by the respective radiation absorption.

Coming back to FIG. 2, it should be mentioned that a hydrostatic pressure sensor 16 is represented there on the pump inlet branch 5, and this sensor is connected to a suitable processing device 17. A pressure sensor may also be provided at the pump outlet. A pressure difference across the pump can also be determined directly by way of this. A temperature sensor 18 which is within the pump casing 6a and which is connected to a processing device 19 is also represented in FIG. 2. The temperature sensor 18 may also be arranged outside the pump in a region subjected to throughflow by the delivered fluid.

Figure 4:
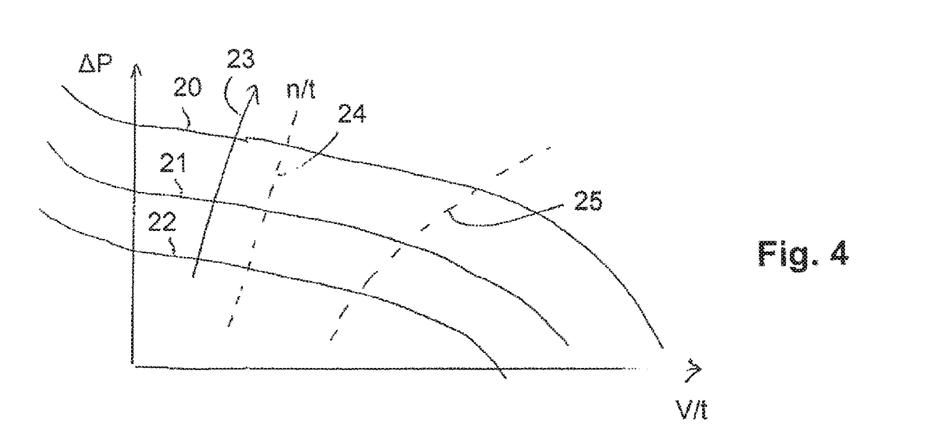
FIG. 4 a typically family of characteristic curves of a pump, with characteristic curves which permit an assignment of a speed and a pressure difference to a volume flow.

FIG. 4 shows a diagram in which the volume flow through the pump in volume per time is plotted on the horizontal axis against the pressure difference across the pump for different speeds of the pump. A characteristic curve family results by way of this, in which, by way of example, three characteristic curves 20, 21, 22 are represented for different speeds. The arrow 23 thus indicates the transition direction between curves of different speeds.

Thus, operating points of the pump (pressure difference between the inlet and outlet the pump as well as the volume flow delivered through the pump) are represented in the form of the characteristic curves for different speeds of the pump. Therein, the speed and the axial bearing position of the rotor are recorded as a representative variable for the pressure difference across the rotor, for determining characteristic curves. As an alternative, the speed and the torque of the pump rotor, measured by the motor current, may also be detected. Measurement points can be interpolated into characteristic curves by way of suitable regression curves. Thus for example the volume flow through the pump can be determined in certain regions of the characteristic curve family from the detected operating parameters, in particular from the speed and the axial bearing position of the rotor, during operation of the pump.

A different method can be selected for certain regions of the characteristic curve family in order to determine the volume flow, since it has been recognised that for certain pump types, regions exist in the characteristic curve family where the assignment between bearing position/pressure difference and the volume flow at a known speed is not unambiguous or at the very least is not clear. The corresponding evaluation method can thus be selected in dependence on the region of the characteristic curve family in which the operating point of the pump is located, thus for example in dependence on the speed and/or the pressure difference across the pump. The respective suitable selection of operating parameters is then chosen, depending on the operating parameters, for control also during operation of the pump on the basis of the stored characteristic curve family.

For example, a part-family of the characteristic curve family, in which part-family the volume flow is not determined solely from the speed and the pressure difference across the rotor or at least not solely from these parameters, is formed in FIG. 4 between the two dashed lines 24 and 25. For example, the torque of the rotor, determined by the current of the electric drive motor of the rotor, and/or the absolute pressure at the inlet and/or the outlet of the pump, may be taken into consideration in the family between the lines 24 and 25. These variables may be evaluated alone or in combination with the speed of rotation, but the bearing position as an indicator for the pressure difference across the rotor may also be included in the evaluation of the volume flow.

The fluid temperature may moreover be detected by a sensor, since it is particularly with blood pumps that the temperature of the blood has a large influence on the viscosity and thus on the operating conditions or operating parameters of the pump.

Figure 5:
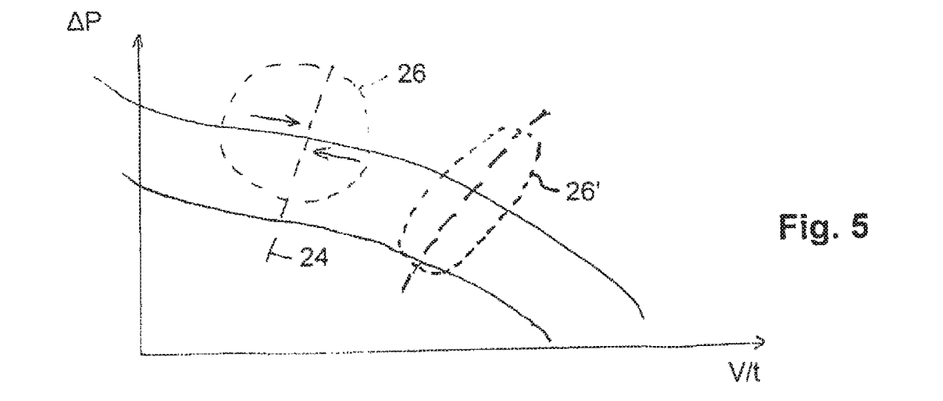
FIG. 5 is a diagram according to FIG. 4 with which an evaluation of the pressure difference across the pump is explained.

FIG. 5 shows the use of several measurement methods in a particular, predefined region which represents a boundary region/transition region of the characteristic curve families and which is indicated by the dashed circle 26. This region lies in the neighbourhood of the separating line 24 between the two regions of the characteristic curve family which demand and permit different measurement methods for determining the volume flow. Several methods for determining the volume flow and/or the pressure difference across the pump may be reliably applied in the predefined region around the separating line 24; the volume flow or the pressure difference across the pump may for example be determined using different captured operating parameters. The viscosity of the delivered fluid, for example of the patient's blood, may be determined by way of comparison of the thus determined values for the volume flow and/or the pressure difference across the pump. Basically, the viscosity can also be determined from the captured, redundant operating parameters even without specific evaluation of the volume flow and/or the pressure difference across the pump.

FIG. 6 shows a blood pump 103 with a rotor 104 which is electromotorically driven by a stator 106 which lies on the pump casing 105. The rotor comprises delivery elements which are not represented in more detail and which axially deliver the blood which flows into the pump tube 105a in the inflow direction 107. The pump tube 105a is part of the pump casing 105. The first sensor device 100, 101, 102 for measuring the oxygen saturation of the blood is fastened, for example screwed, bonded or clamped on the pump tube, in front of the rotor 104 in the flow direction. The first sensor device comprises a first radiation source in the form of a diode 100, as well as a second diode 101 and a phototransistor 102 as a radiation sensor which detects radiation of both diodes. The diodes 100 and 101 can be operated separately, simultaneously or in an alternating manner, in order to send radiation through the blood.

The radiation sensor is operated such that it detects the transmitted light separately in two separate wavelength regions, so that the quotient formation mentioned above is rendered possible.

The first sensor device can be designed as a ring, on which the radiation sources/diodes and the radiation sensor/phototransistor are fastened and which as a whole can be applied onto the pump tube and locked there.

A pump device is schematically represented in FIG. 7 which comprises suitable devices for detecting the operating parameters as well as a first sensor device for determining the oxygen saturation of the blood. Such a pump device comprises a pump 6 with a rotor 34, a magnetic trust bearing 12, a sensor 29 for the bearing strain as well as a motor 27 with an outer-lying stator which drives the pump 6. A speed sensor 33 as well as a current sensor 28 for the motor current are moreover provided. The measured operating parameters are transferred to an analysis device 30 which comprises a control device 31 with a memory device for characteristic curve data. The analysis device 30 moreover comprises a device 32 for determining the viscosity. This exchanges data with the control device 31, so that optimised characteristic curve data can be used in each case with the pump control. The supply of the body of the patient with oxygen can be monitored, assessed and controlled or regulated by way of determining a volume flow in combination with the evaluation of the oxygen saturation of the blood.

An acceleration sensor 108 is moreover arranged in the body of a patient, in particular likewise on the pump, so that a physical activity of a patient and thus a physiological loading or stress can be recognised and put into relation with the measured oxygen saturation of the blood. The acceleration sensor 108 for example can be designed as a semiconductor element which can also be combined with one of the diodes serving as radiation sources, or with a phototransistor serving as a radiation sensor.

The measured values of the oxygen saturation and volume flow can also form the basis for the control of a heart pacemaker and be transmitted to the control unit of a heart pacemaker for this purpose.

Due to the measures described, evaluation of the volume flow through the pump, for example by using a currently determined viscosity, is significantly improved, in particular for those pumps for which an adequate number of operating parameters in certain regions of the characteristic curve family can be acquired. Different measurement possibilities with regard to the blood of a patient are rendered possible by way of the measuring of the oxygen saturation. The integration of the first sensor device into the pump renders the handling simple, even on implantation, and renders reliable the measurement of the oxygen saturation. The first sensor device may not only be designed as an optical measuring device as described, but may make use of any other known measuring method.

The invention claimed is:

1. A system comprising:
    a heart pump including a delivery channel and a delivery device configured to convey blood, the delivery device arranged in the delivery channel;
    an oximeter configured to measure an oxygen saturation of the blood, the oximeter fastened on the heart pump, the oximeter including a ring on which a radiation source and a radiation sensor are fastened;
    a sensor device; and
    a control device connected to the sensor device, wherein the sensor device is configured to determine a volume flow or the control device is configured to determine the volume flow, and wherein the control device is configured to
    determine oxygen flow through the heart pump from the volume flow and the oxygen saturation, and
    control the heart pump based on the oxygen saturation or the oxygen flow through the heart pump.

2. The system of claim 1, wherein the radiation sensor is configured to detect radiation intensity in at least two different wavelength regions, independently of one another.

3. The system of claim 1, wherein a connection path between the radiation source and the radiation sensor traverses a flow direction of the blood in the delivery channel.

4. The system of claim 1, wherein the radiation source and the radiation sensor lie opposite one another on a periphery of a pump tube of the heart pump.

5. The system of claim 1, wherein the sensor device is configured to detect a bearing strain of a magnetic thrust bearing of a pump rotor, and/or detect a torque transmitted onto the pump rotor and/or a rotation speed of the pump rotor.

6. The system of claim 1 wherein the sensor device is configured to detect the volume flow through the heart pump.

7. (Withdrawn - Currently Amended) The system of claim 1, wherein the sensor device is configured to detect the volume flow and/or a pump flow and a rotation speed of a motor configured to drive a pump rotor of the heart pump; and/or wherein the sensor device is configured to detect a bearing strain of a magnetic thrust bearing which mounts the pump rotor, wherein the control device is connected to the sensor device.

8. A method for operation of a heart pump, the method comprising:
    determining an oxygen saturation from blood by an oximeter fastened on the heart pump, the oximeter including a ring on which a radiation source and a radiation sensor is fastened;
    determining a volume flow by a sensor device or a control device in communication with the sensor device;
    determining oxygen flow through the heart pump from the volume flow and the oxygen saturation; and
    controlling the heart pump based on the oxygen saturation or the oxygen flow through the heart pump.

9. The method of claim 8, wherein the controlling comprises regulating and/or controlling a speed and/or the volume flow through the heart pump based on the oxygen saturation and/or the oxygen flow through the heart pump.

10. The method of claim 8 further comprising determining an indicator value from the oxygen saturation, and transmitting the indicator value.

11. The method of claim 8, wherein the heart pump has a pump rotor, and determining the volume flow comprises estimating the volume flow by: detecting a bearing strain of a magnetic thrust bearing of the pump rotor, detecting torque transmitted onto the pump rotor, and/or detecting a rotation speed of the pump rotor.

12. The method of claim 8, wherein determining the oxygen saturation comprises emitting light from the radiation source and receiving the emitted light at the radiation sensor.

13. The method of claim 8, wherein the radiation source includes a plurality of radiation sources, and the radiation sensor includes a plurality of radiation sensors, wherein the radiation sources and the radiation sensors are fastened to the ring, and wherein the radiation sources and the radiation sensors are located on a periphery of a pump tube of the heart pump.

14. The method of claim 8, wherein the heart pump has a delivery channel, and wherein a connection path between the radiation source and the radiation sensor traverses a flow direction of the blood in the delivery channel.

15. The method of claim 8, wherein the heart pump has a delivery channel, and wherein a connection path between the radiation source and the radiation sensor lies perpendicular to a flow direction of the blood in a delivery channel.

\* \* \* \* \*